United States Patent [19]

Zapata et al.

[11] Patent Number: 5,261,457
[45] Date of Patent: Nov. 16, 1993

[54] PNEUMATIC CONTROL VALVE

[75] Inventors: Richard Zapata, Sassenage; Jean Arnault, Saint Nazaire les Eymes, both of France

[73] Assignee: L'Air Liquide, Societe Anonyme pour l'Etude et l'Exploitation des Procedes Georges Claude, Paris, France

[21] Appl. No.: 827,153

[22] Filed: Jan. 27, 1992

[30] Foreign Application Priority Data

Feb. 14, 1991 [FR] France ................... 91 01736

[51] Int. Cl.⁵ ............................................. F16K 31/04
[52] U.S. Cl. .................................. 137/625.65; 251/250
[58] Field of Search ................ 137/625.65; 251/250

[56] References Cited

U.S. PATENT DOCUMENTS

| | | | |
|---|---|---|---|
| 2,656,144 | 10/1953 | Frantz . | |
| 2,661,762 | 12/1953 | Bryant . | |
| 3,888,278 | 6/1975 | Hawks | 137/625.65 |
| 3,996,965 | 12/1976 | Peters | 137/625.66 |
| 4,133,348 | 1/1979 | Spitz | 137/625.65 |
| 4,579,145 | 4/1986 | Leiber et al. | 137/625.65 |
| 4,759,386 | 7/1988 | Grouw, III | 251/250 X |

FOREIGN PATENT DOCUMENTS 46877  4/1989  Fed. Rep. of Germany .
11468  of 1911 United Kingdom .

Primary Examiner—John C. Fox
Attorney, Agent, or Firm—Young & Thompson

[57] ABSTRACT

The valve slide, which is slidably mounted in a housing of a valve member, comprises a central part including a shaped part cooperating with a first joint between a first zone and a second zone of the housing, and an end part including a peripheral joint between the second zone and a third zone, the three zones being in communication with three respective circuits of a pneumatic distribution block.

8 Claims, 1 Drawing Sheet

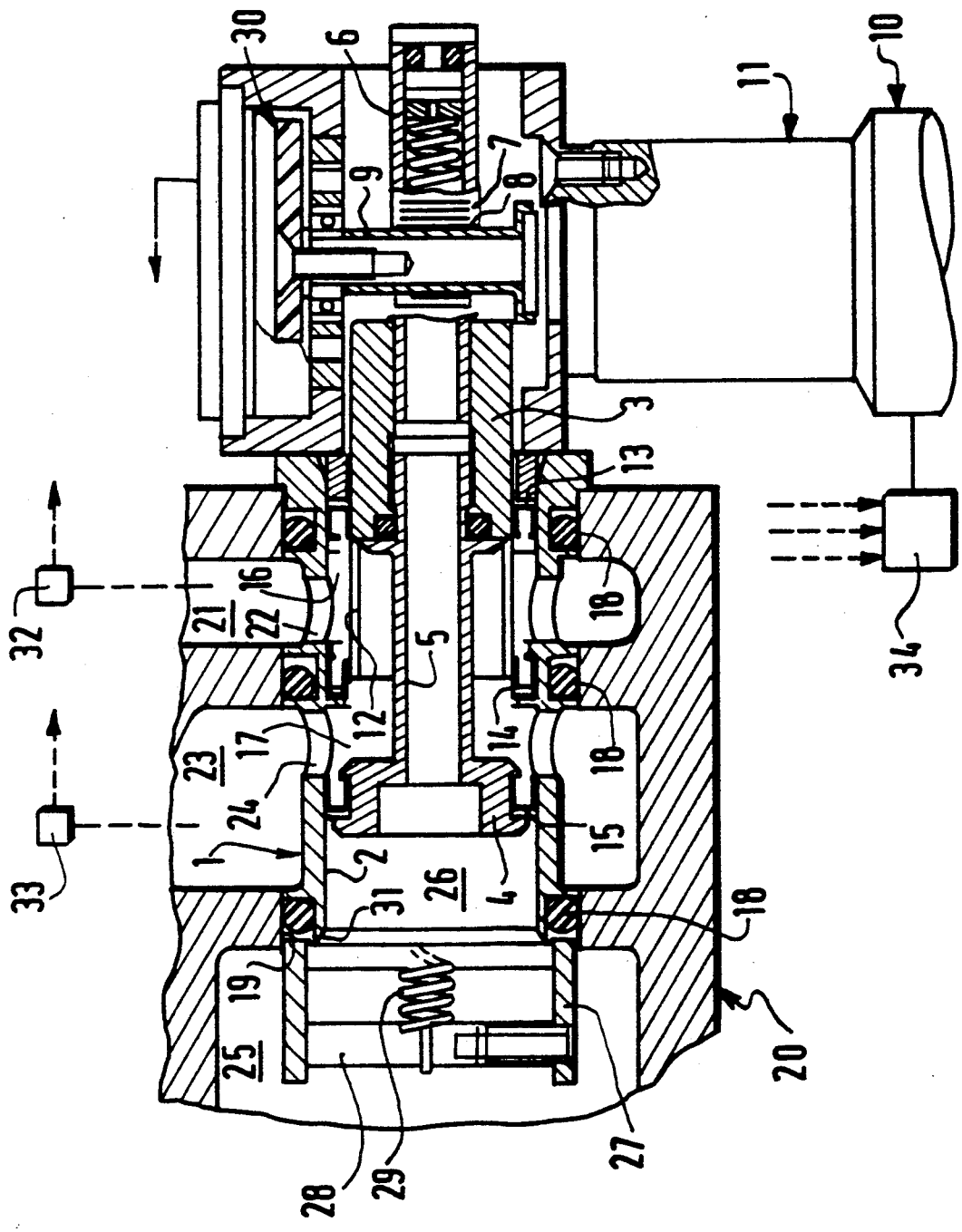

PNEUMATIC CONTROL VALVE

BACKGROUND OF THE INVENTION a) Field of the Invention

The present invention relates to a pneumatic control valve, of the type comprising a valve member defining an interior housing of substantially uniform cross-section in which a valve slide is slidably mounted, the valve slide having a shaped part cooperating with at least a first joint carried by the valve member to establish a modulable communication between a first and a second zone of the housing, and means for controling the valve slide.

SUMMARY OF INVENTION b) Description of Prior art

It is an object of the present invention to propose a valve of the above-mentioned type which is of simple and strong design, is capable of extended miniaturization, having reduced inertia and enabling a three-way control with two outlets of proportional type.

For this purpose, according to a characteristic of the invention, the valve slide comprises a center part in which the shaped part is provided, and an end part in impervious sliding engagement with the housing and separating the second zone from a third zone in the housing.

According to a more specific characteristic of the invention, the housing includes, opposite the first zone, an end part of enlarged interior cross-section in which the end part of the valve slide is received in an end stroke position of the slide, where communication is established between the second and third zone.

According to yet another particular characteristic of the invention, the joints associated with the valve slide are of the metalloplastic expander type.

BRIEF DESCRIPTION OF DRAWINGS

Other characteristics and advantages of the present invention will appear from the description which follows of an embodiment, given by way of illustration but without limititation, with reference to annexed drawings, in which:

the single FIGURE is a schematic illustration of a three-way pneumatic control valve according to the invention.

DESCRIPTION OF PREFERRED EMBODIMENTS

The valve according to the invention comprises a valve member 1, typically of tubular shape, defining an internal housing 2 typically a bore, in which, a valve slide assembly is slidably mounted, comprising a central cylindrical part 3 and an end cylindrical part 4, connected to the central part by means of a tubular rod 5. In the example illustrated, the valve slide assembly additionally includes a rear rod section 6 of quadratic cross-section in which one of the faces comprises a toothed rack 7 meshing with a pinion 8 carried by a shaft 9 which is rotatably driven by means of an electric motor 10, of the continous current and rapid acceleration type, via a motoreducer 11.

According to an aspect of the invention, the central part 3 of the valve slide includes a tubular end zone and ports 12 formed in the wall thereof, said ports having predetermined shapes depending on required control performances. The portion of the central part 3 which is not provided with ports is in impervious sliding engagement with a metalloplastic joint 13 mounted in a groove of bore 2 while the end part provided with ports 12 is engaged with another joint 14 also mounted in a groove bore 2. The end part 4 of the valve slide carries a peripheral joint 15 in contact with the wall of the bore 2. Joints 13 and 14 define, in bore 2, a first zone 16 while joint 14 and joint 15 define in bore 2 a second zone 17, ports 12 defining a modulable communication, depending on the position of valve slide 3, between these two zones 16 and 17.

According to an aspect of the invention, in order to provide for a better durability and a reduced inertia of the valve, joints 13, 14 and 15 are semi-rigid metalloplastic expander joints, such as those commercialized under the designation "Spring-ring" by Fluorocarbon or "Enerseal" by Advanced Products.

Typically, valve body 1 is mounted in a bore 19 of a distribution block 20, O'ring 18 being disposed therebetween, a first duct or inlet duct 21 being formed in the distribution block 20, to be in permanent communication with the first zone 16 by means of a series of openings 22 formed in the wall of valve body 2, a second duct or outlet duct 23, in current communication with second zone 17 by means of a series of openings 24 being formed in the wall of valve body 2, and a third duct or exhaust duct 25 in which opens a third zone 26 defined in the end of the bore 2 by means of the end part 4 of the valve slide assembly.

According to an aspect of the invention, the valve body 2 includes, at the end opposite a motor 10, two lateral arms 27, extending in the third duct 25 and being bridged by means of a rod 28 to which is connected a first end of a helicoidal traction spring 29 extending in the valve slide and whose other end is interiorly fixed in the rear part of rod 6 so as to urge valve slide assembly in a direction towards rod 28 by catching the play of the transmission between motor 10 and the valve slide assembly 3 and thus promoting the controls of positions of the valve slide which are ensured, for example, by means of a potentiometer 30 connected to shaft 9. Spring 29 also enables to place the valve slide 3 in a safety position in case of failure of the control means of this valve slide. In the third zone 26 of the bore 2, the wall of the latter outwardly extends by forming a beveled edge 31 through which the joint 15 of the end part 4 may pass in a stroke end (towards the left on the drawing) of the valve slide assembly, thereby establishing a progressive communication between a second zone 17 and the third zone 26 while, in this position, the ports 12 are past joint 14 which thus insulates the first zone 16 from the second 17.

The pneumatic control valve according to the invention is particularly applicable in a system of supplying breathing gas to an aircraft passenger, the first duct 21 being connected, by means of a feeding duct, to a source of gas containing oxygen, second duct 23, being connected by means of a utilization duct, to the mask of the passenger and the third duct 25 communicating with the surrounding atmosphere. In such a system, pressure pick-ups 32 and 33 detect the pressures in the inlet duct 21 and in the utilization duct 23, the signals originating from the pick-ups 32 and 33 as well as from the potentiometer 30 being sent to an electronic block 34 for controling the electric motor 10.

Although, the present invention has been described with respect to a specific embodiment, it is not limitthereto, but, on the contrary, it is capable of modifications and variants which will be obvious to one skilled in the art.

We claim:

1. For use in a gas circuit, a control valve comprising a housing having an inner recess in which a hollow control slide urged by a tension spring is slidably accommodated, electric actuating means for continuously positioning the control slide in the recess, said actuating means including an electric motor and a rack-and-pinion coupling between the motor and control slide, said inner recess carrying at least a first seal cooperating with the control slide and separating a first zone and second zone in the recess, said control slide having an intermediate portion having a profiled shape and cooperating with the first seal to establish a passage of variable section between the first and second zones depending on the position of the control slide as set by the actuating means, a distal end portion cooperating in sealing sliding engagement with a wall portion of the recess to separate the second zone from a third zone in the recess, and said wall portion of the recess having an end part widening in a direction opposite to the first zone, whereby a modulable communication is established between the second and the third zones when the control slide reaches a stroke end position.

2. The valve of claim 1, wherein fluid communication between the first and second zones is blocked when the control slide reaches said stroke end position.

3. The valve of claim 2, wherein the distal end portion of the control slide carries a second seal cooperating with the wall portion of the recess.

4. The valve of claim 3, wherein the first and second seals are dynamic seals of the metalloplastic expander type.

5. The valve of claim 2, wherein the first zone is connectable to a source of gas under pressure and the second zone is connectable to a user device.

6. The valve of claim 5, wherein the third zone is connectable to a low pressure volume.

7. The valve of claim 5, wherein the source of gas under pressure is a source of a breathing gas.

8. The valve of claim 7, wherein the third zone opens to ambient atmosphere.

* * * * *